(12) United States Patent
Kawana et al.

(10) Patent No.: US 10,300,103 B2
(45) Date of Patent: May 28, 2019

(54) LACTIC-ACID-BACTERIA-CONTAINING COMPOSITION, ORAL PHARMACEUTICAL COMPOSITION FOR TREATING HPV INFECTION AND/OR HPV-ASSOCIATED TUMORS, AND MUCOSAL IMMUNITY-INDUCING AGENT

(71) Applicants: The University of Tokyo, Tokyo (JP); JAPAN HEALTH SCIENCES FOUNDATION, Tokyo (JP)

(72) Inventors: Kei Kawana, Tokyo (JP); Shizunobu Igimi, Tokyo (JP)

(73) Assignees: The University of Tokyo, Bunkyo-ku, Tokyo (JP); Japan Health Sciences Foundation, Chiyoda-ku, Tokyo (JP)

( * ) Notice: Subject to any disclaimer, the term of this patent is extended or adjusted under 35 U.S.C. 154(b) by 0 days.

(21) Appl. No.: 15/547,273

(22) PCT Filed: Jan. 28, 2016

(86) PCT No.: PCT/JP2016/052481
§ 371 (c)(1),
(2) Date: Jul. 28, 2017

(87) PCT Pub. No.: WO2016/121865
PCT Pub. Date: Aug. 4, 2016

(65) Prior Publication Data
US 2018/0008663 A1    Jan. 11, 2018

(30) Foreign Application Priority Data
Jan. 30, 2015    (JP) .................................. 2015-017407

(51) Int. Cl.
| | | |
|---|---|---|
| A61K 38/00 | (2006.01) | |
| C12N 1/20 | (2006.01) | |
| A61K 38/02 | (2006.01) | |
| C12R 1/245 | (2006.01) | |
| A61K 39/12 | (2006.01) | |
| C07K 14/025 | (2006.01) | |
| C12N 15/09 | (2006.01) | |
| A61P 31/20 | (2006.01) | |
| A61P 35/00 | (2006.01) | |
| C12N 7/00 | (2006.01) | |

(52) U.S. Cl.
CPC .............. *A61K 38/02* (2013.01); *A61K 39/12* (2013.01); *A61P 31/20* (2018.01); *A61P 35/00* (2018.01); *C07K 14/025* (2013.01); *C12N 1/20* (2013.01); *C12N 15/09* (2013.01); *C12R 1/245* (2013.01); *A23Y 2220/00* (2013.01); *C12N 7/00* (2013.01)

(58) Field of Classification Search
None
See application file for complete search history.

(56) References Cited

U.S. PATENT DOCUMENTS

| | | |
|---|---|---|
| 2011/0318384 A1 | 12/2011 | Sung et al. |
| 2015/0098959 A1 | 4/2015 | Kei et al. |

FOREIGN PATENT DOCUMENTS

| | | |
|---|---|---|
| EP | 2386645 | 11/2011 |
| JP | 2014-210747 | 11/2014 |

OTHER PUBLICATIONS

Poo, H., et al., "Oral Administration of Human Papillomavirus Type 16 E7 Displayed on Lactobacillus casei Induces E7-Specific Antitumor Effects in C57/BL6 Mice", Int. J. Cancer, 2006, pp. 1702-1709, vol. 119, No. 7.
Sewaki, T., "Generation of Mucosal Vaccine Utilizing Lactobacillus Display System", Journal of the Pharmaceutical Society of Japan, Jun. 2009, pp. 1327-1332, vol. 129, No. 11.
Kawana, K., "Frontier of Cancer Immunotherapy, 11. Development of HPV Molecule-Targeted Cancer Immunotherapy via Mucosa Immunity", Obstetrics & Gynecology, 2014, pp. 210-216, vol. 81, No. 2.
Ribelles, P., et al., "Protection Against Human Papillomavirus Type 16-Induced Tumors in Mice Using Non-Genetically Modified Lactic Acid Bacteria Displaying E7 Antigen at its Surface", Appl. Microbiol. Biotechnol., 2013, pp. 1231-1239, vol. 97, No. 3.
Bermúdez-Humarán, L.G., et al., "An Inducible Surface Presentation System Improves Cellular Immunity Against Human Papillomavirus Type 16 E7 Antigen in Mice after Nasal Administration with Recombinant Lactococci", J. Med. Microbiol., 2004, pp. 427-433, vol. 53.
Bosma, T., et al., "Novel Surface Display System for Proteins on Non-Genetically Modified Gram-Positive Bacteria", Appl. Environ. Microbiol., Jan. 2006, pp. 880-889, vol. 72, No. 1.
Simsek, Ö., et al., "Immobilization of Nisin Producer Lactococcus lactis Strains to Chitin with Surface-Displayed Chitin-Binding Domain", Appl. Microbiol. Biotechnol., 2013, pp. 4577-4587, vol. 97, No. 10.
Raha, A.R., et al., "Cell Surface Display System for Lactococcus lactis: A Novel Development for Oral Vaccine", Appl. Microbiol. Biotechnol., 2005, pp. 75-81, vol. 68, No. 1.
Kawana, K., et al., "Oral Vaccination Against HPV E7 for Treatment of Cervical Intraepithelial Neoplasia Grade 3 (CIN3) Elicits E7-Specific Mucosal Immunity in the cervix of CIN3 patients", Vaccine, Sep. 2014, pp. 6233-6239, vol. 32, No. 47.
Steen, A., et al., "Cell Wall Attachment of a Widely Distributed Peptidoglycan Binding Domain is Hindered by Cell Wall Constituents", J. Biol. Chem., Apr. 2003, pp. 23874-23881, vol. 278.

*Primary Examiner* — Stacy B Chen
(74) *Attorney, Agent, or Firm* — Carmody Torrance Sandak & Hennessey LLP

(57) ABSTRACT

A lactic acid bacterium-containing composition including a lactic acid bacterium having a human papillomavirus (HPV) E7 protein-derived polypeptide on a surface thereof, wherein the HPV E7 protein-derived polypeptide is included in an amount of 0.03 μg to 1.0 μg per $1\times10^8$ lactic acid bacteria; a therapeutic oral pharmaceutical composition for at least one of an HPV infectious disease and an HPV-associated tumor which includes the lactic acid bacterium-containing composition; and a mucosal immunity-inducing agent which includes the lactic acid bacterium-containing composition.

21 Claims, 6 Drawing Sheets

Specification includes a Sequence Listing.

cA      *Lactococcus lactis* IL1403 *AcmA gene*
E7Rb    Human papillomavirus E7 gene

| | |
|---|---|
| *PslpA* | promoter sequence of *Lactobacillus brevis* ATCC1559 S-layer protein |
| ss | secretion signal of *L. brevis* ATCC1559 *prtP gene* |
| E7Rb | Human papillomavirus E7 gene |
| anchor | proteinase sequence of *Lactobacillus casei* |
| amp$^r$ | ampicillin resistant gene of plasmid pGEM-3 |
| ery$^r$ | erythromycin resistant gene of *Staphylococcus aureus* plasmid pE194 |

SEQUENCE LISTING

<160> NUMBER OF SEQ ID NOS: 4

<210> SEQ ID NO 1
<211> LENGTH: 98
<212> TYPE: PRT
<213> ORGANISM: Human papillomavirus type 16

<400> SEQUENCE: 1

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

```
Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
 50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                85                  90                  95

Lys Pro

<210> SEQ ID NO 2
<211> LENGTH: 98
<212> TYPE: PRT
<213> ORGANISM: Human papillomavirus type 16

<400> SEQUENCE: 2

Met His Gly Asp Thr Pro Thr Leu His Glu Tyr Met Leu Asp Leu Gln
 1               5                  10                  15

Pro Glu Thr Thr Gly Leu Tyr Gly Tyr Gly Gln Leu Asn Asp Ser Ser
                20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
 50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                85                  90                  95

Lys Pro

<210> SEQ ID NO 3
<211> LENGTH: 975
<212> TYPE: DNA
<213> ORGANISM: Artificial Sequence
<220> FEATURE:
<223> OTHER INFORMATION: Synthesized Sequence

<400> SEQUENCE: 3
tcttctgctg gtacttctaa ttccggtggt tcaacagcta caaataccaa taataattca      60
aatacaagct caaccactta tacagttaaa tctggcgata cactttgggg aatttcgcaa     120
aaatatggaa ttagtgttgc tcaaattcaa agcgcaaaca atcttaaaag tacagtcatc     180
tatattgggc aaaagcttgt attgacaact tcaagttctt cgtctaatac aaatagttca     240
acttcttcag gaaattctgc cggaactaca acgcctacta cttcggtcac tcctgccaaa     300
ccagcttcac agacgacgat taaggttaaa tctggtgata cgctttgggg actctctgtc     360
aaatataaaa cgacgattgc tcaactcaag agttggaatc atttgaattc tgatacaatt     420
ttcattggac aaaacttgat tgtttcacaa tctgccggtt cttcaagttc ttcaacaggt     480
tcaagctcag cctctacgag ttcaacttct aactcttctg cagcttcaaa tacctctatc     540
cataaggttg ttaaaggaga tacgctttgg ggactttcac aaaaatctgg tagcccaatt     600
gcttcaatta aggcttggaa tcatttatca agtgatacca ttttaattgg tcaatatctt     660
cgtattaaag aggatccgat gcatggagat acacctacta tgcatgaata tatgttagat     720
ttgcaaccag agacaactgg tctctacggt tatgggcaat aaatgacag ctcagaggag     780
```

```
gaggatgaaa tagatggtcc agctggacaa gcagaaccgg acagagccca ttacaatatt      840
gtaacctttt gttgcaagtg tgactctacg cttcggttgt gcgtacaaag cacacacgta      900
gacattcgta ctttggaaga cctgttaatg ggcacactag gaattgtgtg ccccatctgt      960
tctcagaaac cataa                                                       975

<210> SEQ ID NO 4
<211> LENGTH: 624
<212> TYPE: DNA
<213> ORGANISM: Artificial Sequence
<220> FEATURE:
<223> OTHER INFORMATION: Synthesized Sequence

<400> SEQUENCE: 4
atgcatggag atacacctac attgcatgaa atatgttaga tttgcaacca gagacaactg       60
gtctctacgg ttatgggcaa ttaaatgaca gctcagagga ggaggatgaa atagatggtc      120
cagctggaca agcagaaccg gacagagccc attacaatat tgtaaccttt tgttgcaagt      180
gtgactctac gcttcggttg tgcgtacaaa gcacacacgt agacattcgt actttggaag      240
acctgttaat gggcacacta ggaattgtgt gccccatctg ttctcagaaa ccactcgagg      300
cagctgccgt tgaagcggcc aagacagctg gtaaaggcga cgatacaagc ggtactagcg      360
acaaaggcgg cggtcaaggt accccggcgc ccgctccagg cgacacaggt aagaacaaag      420
gcgatgaggg cagccagcct agttctggcg gtaatatccc aacaaagcca gccacaacga      480
cgtcaacgag cacggatgat acgactgatc gtaatggtca acatacatcc ggtaagggag      540
cattacccaa gacagcagag acaactgagc ggccagcgtt tggcttcttg ggtgtcattg      600
tggtcagtct gatgggggta ttag                                             624
```

LACTIC-ACID-BACTERIA-CONTAINING COMPOSITION, ORAL PHARMACEUTICAL COMPOSITION FOR TREATING HPV INFECTION AND/OR HPV-ASSOCIATED TUMORS, AND MUCOSAL IMMUNITY-INDUCING AGENT

TECHNICAL FIELD

The present invention relates to a lactic acid bacterium-containing composition in which a lactic acid bacterium has a human papilloma virus (HPV) E7 protein-derived polypeptide on a surface thereof a therapeutic oral pharmaceutical composition for at least one of an HPV infectious disease and an HPV-associated tumor which includes the lactic acid bacterium-containing composition, and a mucosal immunity-inducing agent which includes the lactic acid bacterium-containing composition.

BACKGROUND ART

Human papilloma viruses (HPVs) are DNA viruses. To date, 100 or more different types of the HPVs have been reported. The HPVs infect the skin (e.g., HPV1 and HPV2) and the mucosal surface (e.g., HPV6 and HPV11) to thereby form benign tumors (warts) existing for from a few months to a few years.

Additionally, 15 types of the HPVs (e.g., HPV16, HPV18, HPV31, HPV33, HPV52, and HPV58) infect the mucosa for a long period of time to thereby cause malignant tumors. Therefore, these are referred to as high-risk HPVs.

Almost 100% of cervical cancers, which have the second highest morbidity next to breast cancers among cancers specific to women, are developed by infection of the HPVs in reproductive organs for a long period of time. It is reported that 530,000 people in the world and 15,000 people in Japan newly develop the cervical cancer every year.

The number of deaths per year from the cervical cancer reaches 270,000 in the world and 3,500 in Japan.

Theoretically speaking, if the HPV infections are completely prevented, the cervical cancer can be eradicated.

The HPV infection has been revealed to be associated with vulvar cancer, anal cancer, oral cancer, vaginal cancer, penile cancer, pharyngeal cancer, and condyloma acuminatum (venereal wart), in addition to the cervical cancer. Therefore, prophylactic vaccines against the HPV infections are thought to be effective for prevention of the above-described cancers and sexually transmitted diseases. However, existing prophylactic HPV vaccines can prevent only two types of the high-risk HPVs.

Among the HPVs, HPV16 and HPV18 account for about 65% of cause for the cervical cancer in Japanese women, especially about 90% in their twenties.

The HPV16 and the HPV18 have also been known to account for a little less than 50% of cause for high-grade lesions of vulvar intraepithelial neoplasia which precede the development of the vulvar cancer, and to be associated with 85% of the development of vaginal intraepithelial neoplasia which may proceed to the vaginal cancer.

Cervical intraepithelial neoplasias (CINs), which are cervical cancer precursor lesions resulting from the HPV infection, occur on the mucosal epithelium of the vaginal portion (a lower half portion or portion extending into the vagina of the cervix). HPV infectious diseases are viral infectious diseases in which the HPVs invade basal cells of the mucosal epithelium (stratified squamous epithelium) due to small injuries caused by sexual practices and proliferate in the squamous epithelium. When the HPVs continuously proliferate in the epithelium for a long period of time, epithelial cells are immortalized and cancerated. This is believed to be the origin of the cervical cancer.

In a developmental process of the cervical cancer, the following changes are thought to occur: when the HPV continuously spreads to the basal cells, some viral genes of the HPVs are inserted to genes of the epithelial cells, and E6 proteins and E7 proteins, which were underexpressed, are continuously increased in expression.

The E6 proteins and the E7 proteins are very lowly expressed in CIN1 (mild dysplasia), which is an infectious feature, but highly expressed in CIN2 (moderate dysplasia) and CIN3 (severe dysplasia), which have been cancerated. Therefore, it is believed to be at the CIN2 stage or later that the E6 proteins and the E7 proteins are continuously increased in expression as described above.

The E6 proteins and the E7 proteins, especially the E7 proteins, of the HPVs are believed to be attractive targets in a development of therapeutic vaccines against HPV-associated cancers. This is because the E7 proteins are highly antigenic in human.

Although there have already been developed some therapeutic vaccines using as antigens the E7 protein of the HPVs (e.g., see NPL 1 and PTL 1), they have not yet been demonstrated to eliminate precursor lesions (the CINs) and cancer cells in the cervixes of patients. Therefore, there is a strong need to develop vaccines which have been demonstrated to have therapeutic effects.

The present inventors have found that E7-specific cellular immune response can be elicited in not only the spleens but also the mucosas in mice through orally administration of vaccines (LacE7) which are made by expressing mutant E7 proteins (SEQ ID NO. 2) in *Lactobacillus casei* followed by subjecting to heat treatment to kill and drying to powder (see NPL 2). The mutant E7 proteins are those in which Asp at position 21, Cys at position 24, and Glu at position 26 involving in binding with Rb proteins are all substituted with Gly in HPV16 E7 proteins.

The present inventors have also been conducting the research regarding combinations of HPV E7 polypeptides and Kampo preparations having revitalizing activity as therapeutic oral pharmaceutical compositions for HPV infectious diseases (see PTL 2).

Based on the previous research by the present inventors, a therapeutic vaccine which exerts some clinical effect is being developed.

However, the therapeutic vaccine can only cause regression from CIN3 (severe dysplasia) to CIN2 (moderate dysplasia) in the stages leading to the development of cervical cancer, and it is difficult for the therapeutic vaccine to achieve the normal state. In order to further improve the clinical effect in patients suffering from at least one of cervical intraepithelial neoplasia and early-stage cervical cancer so as to normalize the cancer, there is a strong need to rapidly provide a therapeutic oral pharmaceutical composition for at least one of an HPV infectious disease and an HPV-associated tumor having a more excellent mucosal immunity-inducibility.

CITATION LIST

Patent Literature

PTL 1: Japanese Patent Application Laid-Open (JP-A) No. 2012-514469
PTL 2: International Publication No. 2013/191225

Non-Patent Literature

NPL 1: H. Poo et al., Int J. Cancer, 2006, vol. 119, pp. 1702-1709

NPL 2: K. Adachi et al., Vaccine, 2010, vol. 28, pp. 2810-2817

SUMMARY OF INVENTION

Technical Problem

The present invention aims to solve the above problems and achieve the following object. An object of the present invention is to provide a lactic acid bacterium-containing composition which has an excellent mucosal immunity-inducibility, and a therapeutic oral pharmaceutical composition for at least one of an HPV infectious disease and an HPV-associated tumor which includes the lactic acid bacterium-containing composition, and a mucosal immunity-inducing agent which includes the lactic acid bacterium-containing composition.

Solution to Problem

Means for solving the above problems are as follows.
<1> A lactic acid bacterium-containing composition including
 a lactic acid bacterium having a human papillomavirus (HPV) E7 protein-derived polypeptide on a surface thereof,
 wherein the HPV E7 protein-derived polypeptide is included in an amount of 0.03 μg to 1.0 μg per $1 \times 10^8$ lactic acid bacteria.
<2> A therapeutic oral pharmaceutical composition for at least one of an HPV infectious disease and an HPV-associated tumor, the composition including
 the lactic acid bacterium-containing composition according to <1>.
<3> A mucosal immunity-inducing agent including
 the lactic acid bacterium-containing composition according to <1>.

Advantageous Effects of Invention

According to the present invention, these can solve the above problems and achieve the above object. That is, the present invention can provide a lactic acid bacterium-containing composition which has an excellent mucosal immunity-inducibility, and a therapeutic oral pharmaceutical composition for at least one of an HPV infectious disease and an HPV-associated tumor which includes the lactic acid bacterium-containing composition, and a mucosal immunity-inducing agent which includes the lactic acid bacterium-containing composition.

Figure 1A:
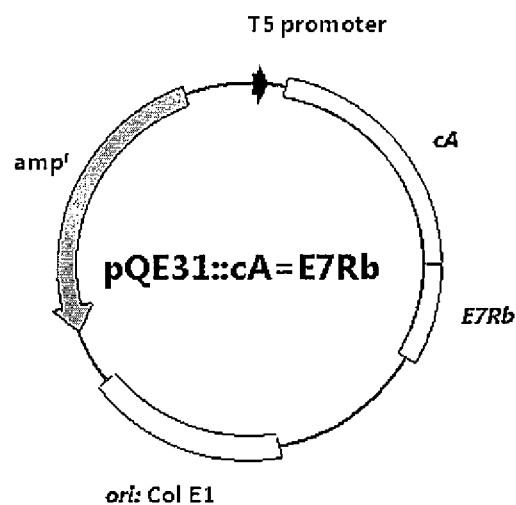
FIG. 1A is a schematic diagram of pQE31::cA=E7Rb in Production Example 1.

DESCRIPTION OF EMBODIMENTS (Lactic Acid Bacterium-Containing Composition)
A lactic acid bacterium-containing composition of the present invention includes at least a lactic acid bacterium having a human papilloma virus (HPV) E7 protein-derived polypeptide on a surface thereof, and, if necessary, further includes other components.
<Lactic Acid Bacterium>
The lactic acid bacterium is not particularly limited and may be appropriately selected depending on the intended purpose, but is preferably a lactic acid bacterium belonging to the genus *Lactobacillus*, more preferably *Lactobacillus casei* because it has been confirmed to induce a type 1 helper T (Th1) cell. The lactic acid bacterium may be used alone or in combination.

The lactic acid bacterium-containing composition may include a lactic acid bacterium having no HPV E7 protein-derived polypeptide on the surface thereof. However, the lactic acid bacterium having a HPV E7 protein-derived polypeptide on the surface thereof is preferably included in a percentage of 80% or more, more preferably 90% or more, particularly preferably 95% or more.
<<HPV E7 Protein-Derived Polypeptide>>
The HPV E7 protein-derived polypeptide is not particularly limited and may be appropriately selected depending on the intended purpose, as long as it is antigenic. The HPV E7 protein-derived polypeptide may be used alone or in combination.

A type of the HPV is not particularly limited and may be appropriately selected depending on the intended purpose, but is preferably HPV16, HPV18, HPV31, HPV33, HPV35, HPV39, HPV45, HPV51, HPV52, HPV56, HPV58, HPV59, HPV68, HPV73, HPV82, HPV26, HPV53, and HPV63, which belong to a high-risk group for cancer, more preferably HPV16 and HPV18, particularly preferably HPV16. An HPV16 E7 protein is a cancer antigen constitutively expressed in cervical cancer and HPV-associated cancers (e.g., anal cancer, pharyngeal cancer, penile cancer, vulvar cancer, and vaginal cancer).

The HPV E7 protein-derived polypeptide may be a full-length HPV E7 protein or an HPV E7 protein in which one to several amino acids are deleted, substituted, or added.

The HPV E7 protein-derived polypeptide may also be derived from a wild-type E7 protein or from a mutant E7 protein.

Among the HPV E7 protein-derived polypeptides, preferable is a mutant E7 protein in which amino acid residues involved in binding with an Rb protein of the E7 protein (i.e., Asp at position 21, Cys at position 24, and Glu at position 26 of a wild-type HPV16 E7 protein (SEQ ID No. 1)) are substituted with other amino acid residues. More preferable is a mutant E7 protein (SEQ ID No. 2) in which Asp at position 21, Cys at position 24, and Glu at position 26 of the wild-type HPV16 E7 protein (SEQ ID No. 1) are all substituted with Gly.

—Amount—

An amount of the HPV E7 protein-derived polypeptide on a surface of the bacterium is not particularly limited and may be appropriately selected depending on the intended purpose, as long as it is 0.03 μg to 1.0 μg per $1 \times 10^8$ lactic acid bacteria. However, the amount is preferably 0.03 μg to 0.3 μg, more preferably 0.06 μg to 0.3 μg, particularly preferably 0.09 μg to 0.3 μg. When the amount falls within the above preferable range, it is advantageous in that a more excellent pharmacological effect (mucosal immunity-inducibility) can be exerted.

A method for measuring the amount of the HPV E7 protein-derived polypeptide on a surface of the bacterium is not particularly limited and may be appropriately selected depending on the intended purpose. Examples thereof include a Flow cytometer (FACS) method using an antibody specific for the HPV E7 protein.

The FACS method can measure an amount of the HPV E7 protein-derived polypeptide on a surface of the bacterium in a sample including an unknown amount of the HPV E7 protein-derived polypeptide by measuring in the same manner as for a sample including a known amount of the HPV E7 protein-derived polypeptide.

<<Aspect>>

The HPV E7 protein-derived polypeptide may be bound on a surface of the lactic acid bacterium (hereinafter may be referred to as "E7 protein-bound type lactic acid bacterium") or expressed on a surface of the lactic acid bacterium (hereinafter may be referred to as "E7 protein-expressed type lactic acid bacterium"). The E7 protein-bound type lactic acid bacterium and the E7 protein-expressed type lactic acid bacterium may coexist with each other.

The lactic acid bacterium may be a living bacterium or a killed bacterium.

A method for killing the bacterium is not particularly limited and may be appropriately selected depending on the intended purpose. Examples thereof include a method in which the bacterium is heated in an autoclave at 80° C. for 5 min.

—E7 Protein-Bound Type Lactic Acid Bacterium—

The E7 protein-bound type lactic acid bacterium may be produced by binding the HPV E7 protein-derived polypeptide, which is produced by a genetic recombination method using a transformed bacterium or a chemical synthesis method, to a surface of the lactic acid bacterium.

The HPV E7 protein-derived polypeptide is preferably produced by the genetic recombination method using a transformed bacterium from the viewpoint of, for example, cost.

A bacterium used as a host in the genetic recombination method is not particularly limited and may be appropriately selected depending on the intended purpose. Examples thereof include yeast, *E. coli, Bacillus subtilis* and a lactic acid bacterium.

An expression vector suitable for expressing in the HPV E7 protein-derived polypeptide in the bacterium is not particularly limited and may be appropriately selected depending on the intended purpose. Examples thereof include pQE31.

A method for transforming the bacterium is not particularly limited and may be appropriately selected from methods known in the art.

The HPV E7 protein-derived polypeptide produced by the transformed bacterium may be purified by appropriately selecting from methods known in the art.

A method for binding the HPV E7 protein-derived polypeptide to a surface of the lactic acid bacterium is not particularly limited and may be appropriately selected from methods known in the art such as covalent binding and electrical binding. However, preferable is a method in which the polypeptide is electrically bound to a surface of the lactic acid bacterium via an anchor protein.

The anchor protein is not particularly limited and may be appropriately selected depending on the intended purpose. Examples thereof include a cell wall-binding protein cA derived from AcmA which is a peptidoglycan hydrolase of *Lactococcus lactis*.

When the HPV E7 protein-derived polypeptide is bound to a surface of the lactic acid bacterium via the anchor protein, the HPV E7 protein-derived polypeptide is preferably fused with the anchor protein to form a fusion protein.

An order of the anchor protein and the HPV E7 protein-derived polypeptide in the fusion protein is not particularly limited and may be appropriately selected depending on the intended purpose. However, the anchor protein and the HPV E7 protein-derived polypeptide are preferably fused in this order. Specific examples thereof include the sequence represented by SEQ ID NO. 3.

A method for electrical binding (hereinafter may be referred to as "immobilization") is not particularly limited and may be appropriately selected depending on the intended purpose. Examples thereof include a method in which a solution including the HPV E7 protein-derived polypeptide is added to and mixed with the lactic acid bacterium.

A mixing time is not particularly limited and may be appropriately selected depending on the intended purpose. Examples thereof include about 1 hour.

In the electrical binding method, pretreatment may be performed.

The pretreatment is not particularly limited and may be appropriately selected depending on the intended purpose. Examples thereof include a heat treatment. The lactic acid bacterium is killed by the heat treatment.

A condition for the heat treatment is not particularly limited and may be appropriately selected depending on the intended purpose. Examples thereof include heating at 100° C. for 30 min.

The heat treatment may be performed on the lactic acid bacterium suspended in trichloroacetic acid (TCA) or the lactic acid bacterium suspended in PBS.

—E7 Protein-Expressed Type Lactic Acid Bacterium—

The E7 protein-bound type lactic acid bacterium may be produced by culturing a lactic acid bacterium which has been transformed with an expression vector containing a nucleic acid coding for the HPV E7 protein-derived polypeptide.

The expression vector is not particularly limited and may be appropriately selected depending on the intended purpose. Examples thereof include pIGM2. The pIGM2 contains the secretion signal of *Lactobacillus brevis* ATCC1559 prtP gene downstream of the promoter sequence of *Lactobacillus brevis* ATCC1559 S-layer protein and further contains the anchor gene derived from *Lactobacillus casei* (proteinase sequence of *L. casei*) downstream thereof.

Another example of the expression vector includes a vector containing a mutated repE gene, a lactic acid bacterium-derived aldolase promoter (Pald), and a polyglutamic acid synthase complex gene selected from the group consisting of pgsB, pgsC, and gsA (see JP-A Nos. 2012-514468 and 2012-514469).

A method for transformation is not particularly limited and may be appropriately selected from methods known in the art.

In the case of the E7 protein-expressed type lactic acid bacterium, a nucleic acid coding for the HPV E7 protein-derived polypeptide is preferably linked to an anchor gene.

The anchor gene is not particularly limited and may be appropriately selected depending on the intended purpose, but is preferably the anchor gene derived from *Lactobacillus casei* (proteinase sequence of *L. casei*).

An order of the nucleic acid coding for the HPV E7 protein-derived polypeptide and the anchor gene is not particularly limited and may be appropriately selected depending on the intended purpose. However, the nucleic acid coding for the HPV E7 protein-derived polypeptide and the anchor gene are preferably linked in this order. Examples thereof include the sequence represented by SEQ ID NO. 4.

A lactic acid bacterium used for the E7 protein-expressed type lactic acid bacterium is not particularly limited and may be appropriately selected depending on the intended purpose, but is preferably *Lactobacillus casei* IGM393 or *Lactobacillus casei* IGM394. The *Lactobacillus casei* IGM394 is a subcultured strain derived from the *Lactobacillus casei* IGM393 and is a mutant strain having a high transformation efficiency. The *Lactobacillus casei* IGM393 and the *Lactobacillus casei* IGM394 have the highest homology to a total genomic sequence of *Lactobacillus casei* BL23.

A method for culturing the E7 protein-expressed type lactic acid bacterium is not particularly limited and may be appropriately selected from methods known in the art.

A method for modifying an expression amount of the HPV E7 protein-derived polypeptide on the surface of the bacterium in the E7 protein-expressed type lactic acid bacterium is not particularly limited and may be appropriately selected depending on the intended purpose. Examples thereof include a method in which a culture solution is adjusted for pH.

As described in Production Example 2 below, the expression amount of the HPV E7 protein-derived polypeptide on a surface of the bacterium can be modified by using a medium that concentration of sodium hydrogen carbonate is varied and therefore pH is adjusted.

A pH of the culturing solution is not particularly limited and may be appropriately selected depending on the intended purpose, but is preferably about pH 7.

When the HPV E7 protein-derived polypeptide is a fusion protein with the anchor protein, an amount of the fusion protein on a surface of the bacterium is not particularly limited and may be appropriately selected depending on the intended purpose, but is preferably 0.1 µg to 3.3 µg, more preferably 0.1 µg to 1.0 µg, further preferably 0.2 µg to 1.0 µg, particularly preferably 0.3 µg to 1.0 µg per $1\times10^8$ lactic acid bacteria. When the amount falls within the above preferable range, it is advantageous in that a more excellent pharmacological effect (mucosal immunity-inducibility) can be exerted.

<Other Components>

Other components in the lactic acid bacterium-containing composition are not particularly limited and may be appropriately selected depending on the intended purpose, as long as they do not impair the effects of the present invention. Examples thereof include a pharmaceutically acceptable carrier. These may be used alone or in combination.

Amounts of the other components in the lactic acid bacterium-containing composition are not particularly limited and may be appropriately selected depending on the intended purpose.

(Therapeutic Oral Pharmaceutical Composition for at Least One of HPV Infectious Disease and HPV-Associated Tumor)

A therapeutic oral pharmaceutical composition for at least one of an HPV infectious disease and an HPV-associated tumor of the present invention includes at least a lactic acid bacterium-containing composition, and, if necessary, further includes other components.

<Lactic Acid Bacterium-Containing Composition>

The lactic acid bacterium-containing composition is the above-described lactic acid bacterium-containing composition of the present invention.

An amount of the lactic acid bacterium-containing composition included in the therapeutic oral pharmaceutical composition for at least one of an HPV infectious disease and an HPV-associated tumor is not particularly limited and may be appropriately selected depending on the intended purpose.

<Other Components>

Other components in the therapeutic oral pharmaceutical composition for at least one of an HPV infectious disease and an HPV-associated tumor are not particularly limited and may be appropriately selected depending on the intended purpose. Examples thereof include a Kampo preparation having a revitalizing activity (immunity-enhancing effect), a mucosal adjuvant, and a pharmaceutically acceptable carrier. These may be used alone or in combination.

—Kampo Preparation Having Revitalizing Activity (Immunity-Enhancing Effect)—

The Kampo preparation having a revitalizing activity (immunity-enhancing effect) is not particularly limited and may be appropriately selected depending on the intended purpose. Examples thereof include Kakkonto, Juzentaihoto, Hochuekkito, Shosaikoto, and Shoseiryuto. These may be used alone or in combination.

—Mucosal Adjuvant—

The mucosal adjuvant is not particularly limited and may be appropriately selected depending on the intended purpose. Preferable examples thereof include those further enhancing humoral immunity and cell-mediated immunity specific for an oral vaccine such as the HPV E7 protein-derived polypeptide by cooperating with the Kampo preparation having a revitalizing activity (immunity-enhancing effect).

Examples of the mucosal adjuvant include a bacterial toxin-derived adjuvant, a synthetic ceramide (αGalCer), a CpG oligonucleotide, SP-C (SURFACTEN), SP-B, IFN-α (wild-type or mutant), a double-strand RNA, and an activity-enhanced TNF mutant. These may be used alone or in combination.

The bacterial toxin-derived adjuvant is not particularly limited and may be appropriately selected depending on the intended purpose. Examples thereof include a cholera toxin (CT)-derived polypeptide, an *E. coli* heat-labile enterotoxin (LT)-derived polypeptide, a verotoxin (VT)-derived polypeptide, a diphteria toxin (DT)-derived polypeptide, and a pertussis toxin (PT)-derived polypeptide.

The bacterial toxin-derived adjuvant may be a wild-type bacterial toxin-derived adjuvant or a mutant bacterial toxin-derived adjuvant. However, preferable is a mutant bacterial toxin-derived adjuvant in which a mutation has introduced in advance in order not to cause a serious side effect in the case of oral administration to human.

—Pharmaceutically Acceptable Carrier—

The pharmaceutically acceptable carrier is not particularly limited and may be appropriately selected from carriers known in the art depending on dosage forms.

Amounts of the other components in the therapeutic oral pharmaceutical composition for at least one of an HPV infectious disease and an HPV-associated tumor are not particularly limited and may be appropriately selected depending on the intended purpose.

<Use>

The therapeutic oral pharmaceutical composition for at least one of an HPV infectious disease and an HPV-associated tumor may be used alone or in combination with pharmaceuticals including other components as active components. The therapeutic oral pharmaceutical composition for at least one of an HPV infectious disease and an HPV-associated tumor may also be used in a state in which it is incorporated in the pharmaceuticals including other components as active components.

<Dosage Form>

A dosage form of the therapeutic oral pharmaceutical composition for at least one of an HPV infectious disease and an HPV-associated tumor is not particularly limited and may be appropriately selected depending on the intended purpose, as long as it can be orally administered. Examples thereof include an oral solid preparation (e.g., a tablet, a coated tablet, a granule, a powder, and a capsule) and an oral solution (e.g., an internal liquid, a syrup, and an elixir). The therapeutic oral pharmaceutical composition for at least one of an HPV infectious disease and an HPV-associated tumor in any of the-above described dosage forms can be produced according to conventional methods.

<Administration>

An administration amount, an administration timing, and an administration target of the therapeutic oral pharmaceutical composition for at least one of an HPV infectious disease and an HPV-associated tumor are not particularly limited and may be appropriately selected depending on the intended purpose.

The administration amount is not particularly limited and may be appropriately selected considering various factors such as age, weight, physical condition, and symptoms of the administration target, and whether pharmaceuticals or drugs including other components as active components are administered.

Suitable examples of the administration target include human.

The HPV-associated tumor is not particularly limited and may be appropriately selected depending on the intended purpose. Examples thereof include cervical cancer, vulvar cancer, anal cancer, oral cancer, vaginal cancer, penile cancer, pharyngeal cancer, and precancerous lesions thereof.

The therapeutic oral pharmaceutical composition for at least one of an HPV infectious disease and an HPV-associated tumor is suitably available for treating at least one of cervical intraepithelial neoplasia and early-stage cervical cancer.

The early-stage cervical cancer includes microinvasive carcinoma.

The therapeutic oral pharmaceutical composition for at least one of an HPV infectious disease and an HPV-associated tumor is suitable for using as a therapeutic vaccine for an HPV infectious disease by administering to a patient suffering from an HPV infectious disease.

(Method for Treating at Least One of HPV Infectious Disease and HPV-Associated Tumor)

The therapeutic oral pharmaceutical composition for at least one of an HPV infectious disease and an HPV-associated tumor can treat at least one of an HPV infectious disease and an HPV-associated tumor in an individual by orally administering to the individual. Therefore, the present invention also relates to a method for treating at least one of an HPV infectious disease and an HPV-associated tumor, the method including orally administering the therapeutic oral pharmaceutical composition for at least one of an HPV infectious disease and an HPV-associated tumor to an individual.

(Mucosal Immunity-Inducing Agent)

The mucosal immunity-inducing agent of the present invention includes at least a lactic acid bacterium-containing composition, and, if necessary, further includes other components.

<Lactic Acid Bacterium-Containing Composition>

The lactic acid bacterium-containing composition is the above-described lactic acid bacterium-containing composition of the present invention.

An amount of the lactic acid bacterium-containing composition included in the mucosal immunity-inducing agent is not particularly limited and may be appropriately selected depending on the intended purpose.

<Other Components>

Other components in the mucosal immunity-inducing agent are not particularly limited and may be appropriately selected depending on the intended purpose. For example, they may be the same as those described in the section titled "Other components" for the therapeutic oral pharmaceutical composition for at least one of an HPV infectious disease and an HPV-associated tumor.

Amounts of the other components included in the mucosal immunity-inducing agent are not particularly limited and may be appropriately selected depending on the intended purpose.

<Use>

The mucosal immunity-inducing agent may be used alone or in combination with pharmaceuticals including other components as active components. The mucosal immunity-inducing agent may also be used in a state in which it is incorporated in the pharmaceuticals including other components as active components.

<Dosage Form>

A dosage form of the mucosal immunity-inducing agent is not particularly limited and may be appropriately selected depending on the intended purpose, as long as it can be orally administered. Examples thereof include an oral solid preparation (e.g., a tablet, a coated tablet, a granule, a powder, and a capsule) and an oral solution (e.g., an internal liquid, a syrup, and an elixir). The mucosal immunity-inducing agent in any of the-above described dosage forms can be produced according to conventional methods.

<Administration>

An administration amount, an administration timing, and an administration target of the mucosal immunity-inducing agent are not particularly limited and may be appropriately selected depending on the intended purpose.

The administration amount is not particularly limited and may be appropriately selected considering various factors such as age, weight, physical condition, and symptoms of the administration target, and whether pharmaceuticals or drugs including other components as active components are administered.

Suitable examples of the administration target include human.

The mucosal immunity-inducing agent can induce an HPV E7 protein-specific cell-mediated immune response in the mucosa.

(Method for Inducing Mucosa Immunity)

The mucosal immunity-inducing agent can induce mucosa immunity in an individual by orally administering to the individual. Therefore, the present invention also relates to a method for inducing mucosa immunity, the method including orally administering the mucosal immunity-inducing agent to an individual.

EXAMPLES

Production Examples and Test Examples of the present invention are described below, but the present invention is not limited thereto in any way.

Comparative Production Example 1: Production of Known LacE7 Preparation

A LacE7 preparation, which was a known preparation, was produced according to the method described in Poo H. et al., Int. J. Immunol., 2006, vol. 119, pp. 1,702-1,709.

Briefly, an HPV16-derived mutant E7 protein which consisted of the amino acid sequence represented by SEQ ID No. 2, that is, in which Asp at position 21, Cys at position 24, and Glu at position 26, which were involved in binding with an Rb protein, of a wild-type E7 protein were all substituted with Gly was introduced via an expression vector into Lactobacillus casei which had been confirmed to induce a type 1 helper T cell (Th1 cell). The resultant recombinant (LacE7) was cultured in a medium and then was killed by heating. The LacE7 was purified from the medium, washed with distilled water several times, and then dried to powder (LacE7 preparation). The resultant preparation was stored at 4° C. until use. The LacE7 preparation was insoluble in an aqueous solvent.

Production Example 1: Production of Mutant E7 Protein-Bound Type Lactic Acid Bacterium A mutant E7 protein-bound type lactic acid bacterium bound on which surface was produced in the following manner. The mutant E7 protein (SEQ ID No. 2) was an HPV E7 protein-derived polypeptide.
<Production of Mutant E7 Protein>
—Construction of Plasmid for Expressing Protein to which Fusion Sequence of cA and Mutant E7 Protein was Inserted—

A protein cA is an anchor protein and was used as a tool for immobilizing the mutant E7 protein-on a surface of a lactic acid bacterium. The cA can immobilize proteins onto peptidoglycan of a gram-positive bacterium via an electric charge and a certain motif and is a cell wall-binding protein derived from AcmA which is a peptidoglycan hydrolase of Lactococcus lactis (Tjibbe Bosma, Rolf Kanninga, Jolanda Neely Sandrine A. L. Audouy, Maarten L. van Roosmalen, Anton Steen, Girbe Buist, Jan Kok, Oscar P. Kuipers, George Robillard, and Kees Leenhouts (2006) Novel Surface Display System for Proteins on Non-Genetically Modified Gram-Positive Bacteria. Appl. Environ. Microbiol. p. 880-889).

The fusion sequence of the cA and the mutant E7 protein (see SEQ ID NO. 3) was inserted into a vector plasmid pQE31 by a conventional method (hereinafter may be referred to as "pQE31::cA=E7Rb," see FIG. 1A).
—Transformation—

As a host for expressing the fusion protein of the cA and the mutant E7 protein, CLEARCOLI® (E. coli BL21DE3 LPS modified strain, Lucigen) was used.

Firstly, CLEARCOLI® was transformed by an electroporation method to thereby introduce pREP4 (invitrogen) thereinto.

Then, the pQE31::cA=E7Rb was introduced into the resultant transformant by a calcium chloride method to thereby obtain E. coli which expressed the fusion protein of the cA and the mutant E7 protein (hereinafter may be referred to as "CLEARCOLI® pQE31::cA=E7Rb, pREP4").
—Expression and Purification of Fusion Protein—

One platinum loop of the E. coli was inoculated into a Luria-Bertani (LB) liquid medium (Difco Laboratories) containing ampicillin (final concentration: 100 µg/mL) and kanamycin (final concentration: 25 µg/mL) and was cultured with shaking at 37° C. overnight.

The thus-cultured E. coli was collected and washed. Then, PBS was added thereto in the same amount as used for culturing. The resultant in an amount equal to ½₀ of that of a LB liquid medium for main culturing was inoculated into the LB liquid medium for main culturing containing ampicillin (final concentration: 100 µg/mL) and kanamycin (final concentration: 25 µg/mL).

The main culture was performed by culturing with shaking at 37° C. When O. D.$_{600}$ was reached 0.5, IPTG was added so as to give a final concentration of 1 mM. Then, the resultant was cultured with shaking at 37° C. for 4 hours to thereby induce expression of the fusion protein.

The E. coli was collected from the thus-induced culture solution. Five milliliters per g of the E. coli of Lysis buffer (100 mM $NaH_2PO_4$, 10 mM Tris.Cl, 8 M Urea, pH 8) was added thereto and then gently stirred at room temperature for 1 hour. The resultant was centrifuged at 10,000×g for 30 min at 4° C. and then the supernatant was collected.

Four milliliters of the thus-collected supernatant was gently mixed at room temperature for 40 min with 1 mL of TALON® Metal Affinity Resin (Clontech) which had been equilibrated with Lysis buffer. The resultant mixed solution of the supernatant and the resin was transferred to a Polypropylene columns (QIAGEN) to thereby remove the supernatant. The resultant was washed twice with 4 mL of Wash buffer (100 mM $NaH_2PO_4$, 10 mM Tris.Cl, 8 M Urea, pH 6.3) and a His-tagged fusion protein was eluted with Elution buffer 1 (100 mM $NaH_2PO_4$, 10 mM Tris.Cl, 8 M Urea, 150 mM Imidazole, pH 5.9) and Elution buffer 2 (100 mM $NaH_2PO_4$, 10 mM Tris.Cl, 8 M Urea, 300 mM Imidazole, pH 4.5).

The thus-collected protein solution was desalinized by dialysis and concentrated by ultrafiltration using ULTRA-CEL®-10k (Merck Millipore).

The concentration of protein in thus-concentrated protein solution was measured by QUICK START™ Bradford Protein Assay (BIO-RAD) and then the solution was stored at −80° C. until use.
—Confirmation of Fusion Protein by Western Blotting—

In the main culture described in the section "—Expression and purification of fusion protein—," the resultant culture solution which had been added with IPTG and cultured at 37° C. for 4 hours was centrifuged at 10,000×g for 3 min and then the E. coli was collected therefrom. The supernatant was discarded. The resultant pellet was suspended in 100 µL of 1×SDS-PAGE sample buffer. The thus-suspended suspension liquid was heated at 100° C. for 5 min.

The thus-heated suspension liquid was subjected to electrophoresis by SDS-PAGE and transferred onto a PVDF membrane (EDM Millipore).

The thus-transferred membrane was incubated at room temperature for 1 hour in a primary antibody solution (1% BSA, 0.05% Tween 20 in PBS (−), mouse anti-His IgG (Anti-His-tag mAb, MEDICAL & BIOLOGICAL LABORATORIES CO., LTD.) (1:2,000)).

Thereafter, the membrane was washed twice with PBST.

Then, the membrane was incubated at room temperature for 1 hour in a secondary antibody solution (1% BSA, 0.05% Tween 20 in PBS (−), goat anti-mouse IgG HRP (Anti-Mouse IgG (whole molecule)-Peroxidase antibody produced in goat, SIGMA-ALDRICH) (1:10,000)).

Thereafter, the membrane was washed twice with PBST.

Then, an expression of the intended fusion protein was confirmed by detection of bands by ECL Plus (GE Health care Life Science) with Chemi doc (Bio-Rad Laboratories).

<Binding to Surface of Lactic Acid Bacterium>

The fusion protein of the cA and the mutant E7 protein was bound to a surface of a lactic acid bacterium (hereinafter may be referred to as "immobilization") in the following manner with reference to Tjibbe Bosma, Rolf Kanninga, Jolanda Neef, Sandrine A. L. Audouy, Maarten L. van Roosmalen, Anton Steen, Girbe Buist, Jan Kok, Oscar P. Kuipers, George Robillard, and Kees Leenhouts (2006) Novel Surface Display System for Proteins on Non-Genetically Modified Gram-Positive Bacteria. Appl. Environ. Microbiol. p. 880-889.

—Culturing of Lactic Acid Bacterium—

As the lactic acid bacterium, *Lactobacillus casei* IGM393 which had previously been confirmed to have an adjuvant effect as an antigen carrier (Kajikawa A, Igimi S (2010) Innate and acquired immune responses induced by recombinant *Lactobacillus casei* displaying flagellin-fusion antigen on the cell-surface. Vaccine 28: 3409-3415) was used.

The lactic acid bacterium was statically cultured at 37° C. overnight in a Mann-Rogosa-Sharp (MRS) liquid medium (Difco Laboratories). The lactic acid bacterium was collected from the resultant culture solution and washed twice with PBS.

—Pretreatment for Immobilization—

For pretreatment for the immobilization, two kinds of the lactic acid bacteria, i.e., "the lactic acid bacterium treated with trichloroacetic acid (TCA) (hereinafter may be referred to as "with TCA treatment") and "the lactic acid bacterium treated with PBS (hereinafter may be referred to as "without TCA treatment") were prepared.

The lactic acid bacterium was treated with TCA by re-suspending the bacterium in 10% TCA in an amount of 0.2 times as much as that of the culture solution, heating at 100° C. for 30 min, and washing with PBS three times.

The lactic acid bacterium was treated with PBS by re-suspending the bacterium in PBS in an amount of 0.2 times as much as that of the culture solution, heating at 100° C. for 30 min, and washing with PBS three times.

—Immobilization—

The fusion protein was added in an amount of 1.0 µg, 0.3 µg, 0.1 µg, or 0.03 µg (corresponding to 0.3 µg, 0.09 µg, 0.03 µg, or 0.009 µg in terms of the mutant E7 protein, respectively) per $1.0 \times 10^8$ pretreated lactic acid bacteria. The resultant was mixed in a PBS solution containing the fusion protein for 1 hour. As a result, the fusion protein was electrically bound to a surface of the lactic acid bacterium.

After the mixing, the resultant was washed with PBS three times and stored at −80° C. until use.

Thus, the below-described mutant E7 protein-bound type lactic acid bacteria were obtained:

(1) A mutant E7 protein-bound type lactic acid bacterium on which surface 0.3 µg of the mutant E7 protein was bound per $1.0 \times 10^8$ lactic acid bacteria (with TCA treatment);

(2) A mutant E7 protein-bound type lactic acid bacterium on which surface 0.09 µg of the mutant E7 protein was bound per $1.0 \times 10^8$ lactic acid bacteria (with TCA treatment);

(3) A mutant E7 protein-bound type lactic acid bacterium on which surface 0.03 µg of the mutant E7 protein was bound per $1.0 \times 10^8$ lactic acid bacteria (with TCA treatment);

(4) A mutant E7 protein-bound type lactic acid bacterium on which surface 0.009 µg of the mutant E7 protein was bound per $1.0 \times 10^8$ lactic acid bacteria (with TCA treatment);

(5) A mutant E7 protein-bound type lactic acid bacterium on which surface 0.3 µg of the mutant E7 protein was bound per $1.0 \times 10^8$ lactic acid bacteria (without TCA treatment);

(6) A mutant E7 protein-bound type lactic acid bacterium on which surface 0.09 µg of the mutant E7 protein was bound per $1.0 \times 10^8$ lactic acid bacteria (without TCA treatment);

(7) A mutant E7 protein-bound type lactic acid bacterium on which surface 0.03 µg of the mutant E7 protein was bound per $1.0 \times 10^8$ lactic acid bacteria (without TCA treatment); and (8) A mutant E7 protein-bound type lactic acid bacterium on which surface 0.009 µg of the mutant E7 protein was bound per $1.0 \times 10^8$ lactic acid bacteria (without TCA treatment).

<FACS Analysis>

The mutant E7 protein-bound type lactic acid bacteria of (1) to (8) were fluorescently labeled with an antibody specific for the HPV E7 protein and then confirmed for immobilization by Flow cytometer (FACS, BD).

Specifically, each of the mutant E7 protein-bound type lactic acid bacteria was invertedly mixed (room temperature, 60 min) in 0.5 mL of a primary antibody solution (1% BSA, 0.05% Tween 20 in PBS (−), anti-HPV16 E7 mouse IgG (HPV Type 16 E7 Protein antibody [289-17013 (TVG-701Y)], GeneTbx) (1:1,000)). Thereafter, the resultant was centrifuged (15,000×g, 3 min) and then washed twice with PBS (−). Then, the resultant was invertedly mixed with shading (room temperature, 60 min) in 0.5 mL of a secondary antibody solution (1% BSA, 0.05% Tween 20 in PBS (−), anti-mouse IgG Alexa Fluor 488 (Alexa Fluor® 488 goat anti-mouse IgG (H+L), Life technologies) (1:500)). Thereafter, the resultant was centrifuged (15,000×g, 3 min) and then washed twice with PBS (−).

Thereafter, the resultant was added with PBS (−) to a volume of 0.6 mL and subjected to FACS to thereby detect fluorescence.

Note that, those prepared in the same manner except that the fusion protein was not used was used as a negative control.

Figure 1B:
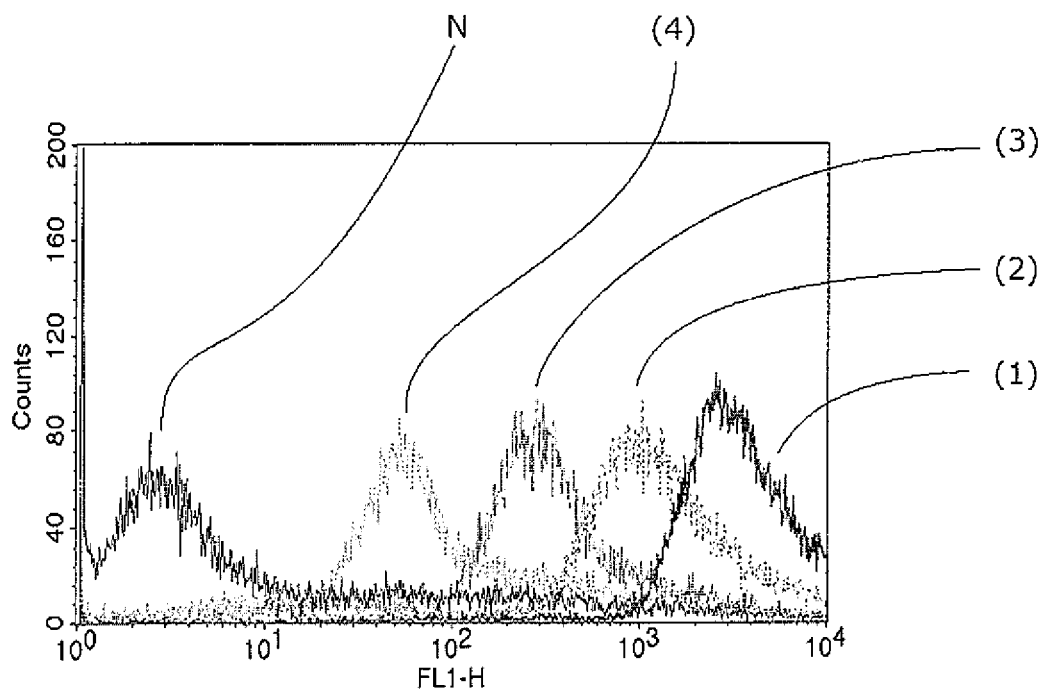
FIG. 1B is Graph-1 illustrating the result of the FACS analysis in Production Example 1.
Figure 1C:
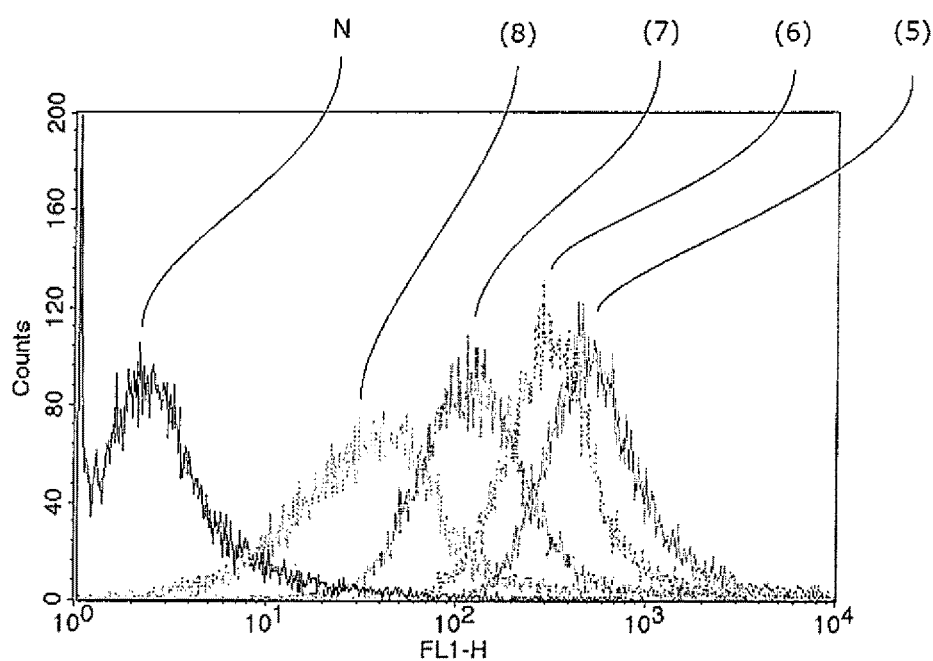
FIG. 1C is Graph-2 illustrating the result of the FACS analysis in Production Example 1.

The results are illustrated in FIGS. 1B and 1C.

In FIG. 1B, "N" represents the result of the negative control, "(1)" represents the result of the mutant E7 protein-bound type lactic acid bacterium on which surface 0.3 µg of the mutant E7 protein was bound per $1.0 \times 10^8$ lactic acid bacteria (with TCA treatment), "(2)" represents the result of the mutant E7 protein-bound type lactic acid bacterium on which surface 0.09 µg of the mutant E7 protein was bound per $1.0 \times 10^8$ lactic acid bacteria (with TCA treatment), "(3)" represents the result of the mutant E7 protein-bound type lactic acid bacterium on which surface 0.03 µg of the mutant E7 protein was bound per $1.0 \times 10^8$ lactic acid bacteria (with TCA treatment), and "(4)" represents the result of mutant E7 protein-bound type lactic acid bacterium on which surface 0.009 µg of the mutant E7 protein was bound per $1.0 \times 10^8$ lactic acid bacteria (with TCA treatment).

In FIG. 1C, "N" represents the result of the negative control, "(5)" represents the result of the mutant E7 protein-bound type lactic acid bacterium on which surface 0.3 µg of the mutant E7 protein was bound per $1.0 \times 10^8$ lactic acid bacteria (without TCA treatment), "(6)" represents the result of the mutant E7 protein-bound type lactic acid bacterium on which surface 0.09 µg of the mutant E7 protein was bound per $1.0\times10^8$ lactic acid bacteria (without TCA treatment), "(7)" represents the result of the mutant E7 protein-bound type lactic acid bacterium on which surface 0.03 μg of the mutant E7 protein was bound per $1.0\times10^8$ lactic acid bacteria (without TCA treatment), and "(8)" represents the result of the mutant E7 protein-bound type lactic acid bacterium on which surface 0.009 μg of the mutant E7 protein was bound per $1.0\times10^8$ lactic acid bacteria (without TCA treatment).

For the results of FIGS. 1B and 1C, it was indicated that fluorescence intensity was enhanced with an increase in the amount of the mutant E7 protein.

Note that, when the amount of the mutant E7 protein was 0.9 μg per $1.0\times10^8$ lactic acid bacteria, a similar result was obtained to that in the case where the mutant E7 protein was 0.3 μg per $1.0\times10^8$ lactic acid bacteria. Therefore, the amount of the mutant E7 protein to be bound to the surface of the bacterium was found to be saturated at about 0.3 μg.

Figure 1D:
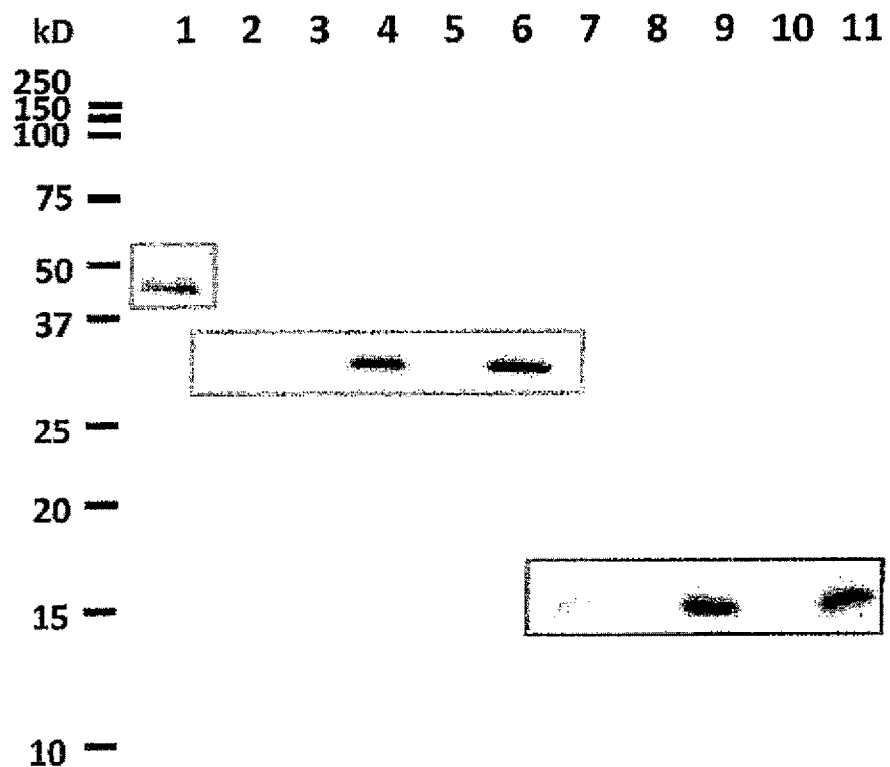
FIG. 1D is an image illustrating one exemplary result of the Western blotting for various proteins.

Note that, one exemplary Western blotting result of proteins described below is illustrated in FIG. 1D.
[Protein]
His-tagged fusion protein of cA and mutant E7 protein (48 kDa);
His-tagged cA (33 kDa); and
His-tagged mutant E7 protein (15 kDa).

In FIG. 1D, "1" represents the result of the "His-tagged fusion protein of cA and mutant E7 protein," "2" represents the result of the "His-tagged cA," "3" and "5" represents the result of a "sample prepared from *E. coli* prior to induction of expression of the His-tagged cA," "4" and "6" represents the result of a "sample prepared from *E. coli* after induction of expression of the His-tagged cA," "7" represents the result of the "His-tagged mutant E7 protein," "8" and "10" represents the result of a "sample prepared from *E. coli* prior to induction of expression of the His-tagged mutant E7 protein," "9" and "11" represents the result of a "sample prepared from *E. coli* after induction of expression of the His-tagged mutant E7 protein."

Production Example 2: Production of Mutant E7 Protein-Expressed Type Lactic Acid Bacterium A mutant E7 protein-bound type lactic acid bacterium on which surface the mutant E7 protein (SEQ ID No. 2), which was an HPV E7 protein-derived polypeptide, was expressed was produced in the following manner.

Figure 2A:
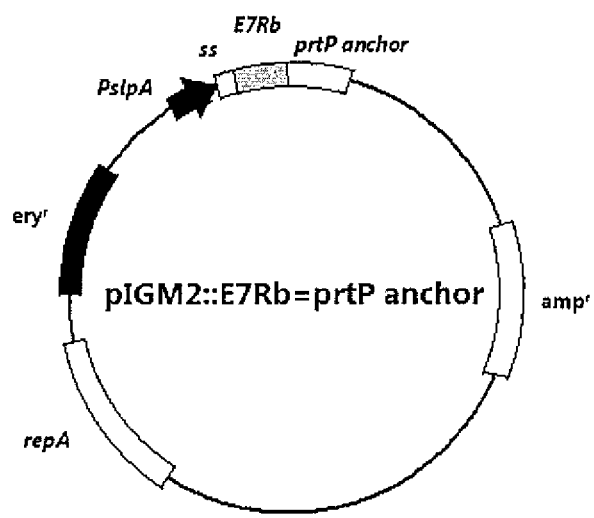
FIG. 2A is a schematic diagram of pIGM2::E7Rb=prtP anchor in Production Example 2.

Using, as a vector plasmid, pIGM2 (Kajikawa Akinobu, Eiko Ichikawa, and Shizunobu Igimi (2010) Development of a Highly Efficient Protein-Secreting System in Recombinant *Lactobacillus casei*. J. Microbiol. Biotechnol., 20(2), 375-382), a vector plasmid in which a sequence coding for the mutant E7 protein (SEQ ID NO. 2) and an anchor gene derived from *Lactobacillus casei* (proteinase sequence of *L. casei*) were linked in this order (SEQ ID NO. 4) was inserted (hereinafter may be referred to as "pIGM2::E7Rb=prtP anchor") was produced (see FIG. 2A).

A terminator sequence was removed from the vector plasmid. The resultant was introduced in *Lactobacillus casei* IGM394 by an electroporation method (hereinafter may be referred to as "*L. casei* IGM394 [pEK7::E7Rb]").

As a negative control, *Lactobacillus casei* IGM394 strain to which a vector plasmid was introduced was produced in the same manner as described above, except that the sequence coding for the mutant E7 protein (SEQ ID NO. 2) and an anchor gene derived from *Lacotobacillus casei* (proteinase sequence of *L. casei*) were linked in this order (SEQ ID NO. 4) was not inserted in the vector plasmid (hereinafter may be referred to as "*L. casei* IGM394 [pLP empty]").

The lactic acid bacterium was seeded in a liquid medium (MRSE) which was Mann-Rogosa-Sharp (Difco Laboratories) supplemented with 5 μg/mL of Em and then cultured at 37° C. overnight (about 14 hours). The lactic acid bacterium was collected from the thus-cultured solution (5,000 g×10 min) and washed once with PBS (5,000 g×10 min). PBS was added thereto to thereby adjust a concentration of the resultant cell suspension liquid to $1\times10^9$ CFU/mL.

The thus-adjusted cell suspension liquid was seeded to 1 L of MRSE ((i) with no addition of $NaHCO_3$, pH 6.4, (ii) with addition of 10 mM $NaHCO_3$, pH 6.8, or (iii) with addition of 25 mM $NaHCO_3$, pH 7.1) in an amount equal to 10% of the MRSE ($1\times10^8$ CFU/mL). The resultant was cultured at 37° C. for about 5 hours with gentle stirring under an anaerobic condition (using ANAEROPACK).

Note that, the lactic acid bacterium serving as the negative control was cultured in (i) MRSE with no addition of $NaHCO_3$.

The lactic acid bacterium was collected from the thus-cultured solution (5,000 g×10 min) and washed once with PBS (5,000 g×10 min). Thirty milliliters of PBS was added thereto to thereby adjust a final concentration of the resultant cell suspension liquid to $7.5\times10^9$ cells/mL (OD≈7.5). Note that, the number of the lactic acid bacterium was counted with a hemocytometer.

The cell suspension liquid was autoclaved at 80° C. for 5 min to kill the bacteria. Also, the bacteria which had not autoclaved were used as a living bacterial sample.

Thus, the below-described mutant E7 protein-expressed type lactic acid bacteria were obtained:
(i-1) A mutant E7 protein-expressed type lactic acid bacterium which had been cultured in MRSE with no addition of $NaHCO_3$ (pH 6.4) and killed;
(i-2) A mutant E7 protein-expressed type lactic acid bacterium which had been cultured in MRSE with no addition of $NaHCO_3$ (pH 6.4) and not killed;
(ii-1) A mutant E7 protein-expressed type lactic acid bacterium which had been cultured in MRSE with addition of 10 mM $NaHCO_3$ (pH 6.8) and killed;
(ii-2) A mutant E7 protein-expressed type lactic acid bacterium which had been cultured in MRSE with addition of 10 mM $NaHCO_3$ (pH 6.8) and not killed;
(iii-1) A mutant E7 protein-expressed type lactic acid bacterium which had been cultured in MRSE with addition of 25 mM $NaHCO_3$ (pH 7.1) and killed; and
(iii-2) A mutant E7 protein-expressed type lactic acid bacterium which had been cultured in MRSE with addition of 25 mM $NaHCO_3$ (pH 7.1) and not killed.
<FACS Analysis>

The mutant E7 protein-expressed type lactic acid bacteria of (i-1), (ii-1), and (iii-1) and the negative control were subjected to the FACS analysis in the same manner as in the Production Example 1 to thereby confirm the degree of expression of the mutant E7 protein on the surfaces of the bacteria per $1.0\times10^8$ lactic acid bacteria. The results are illustrated in FIG. 2B.

Figure 2B:
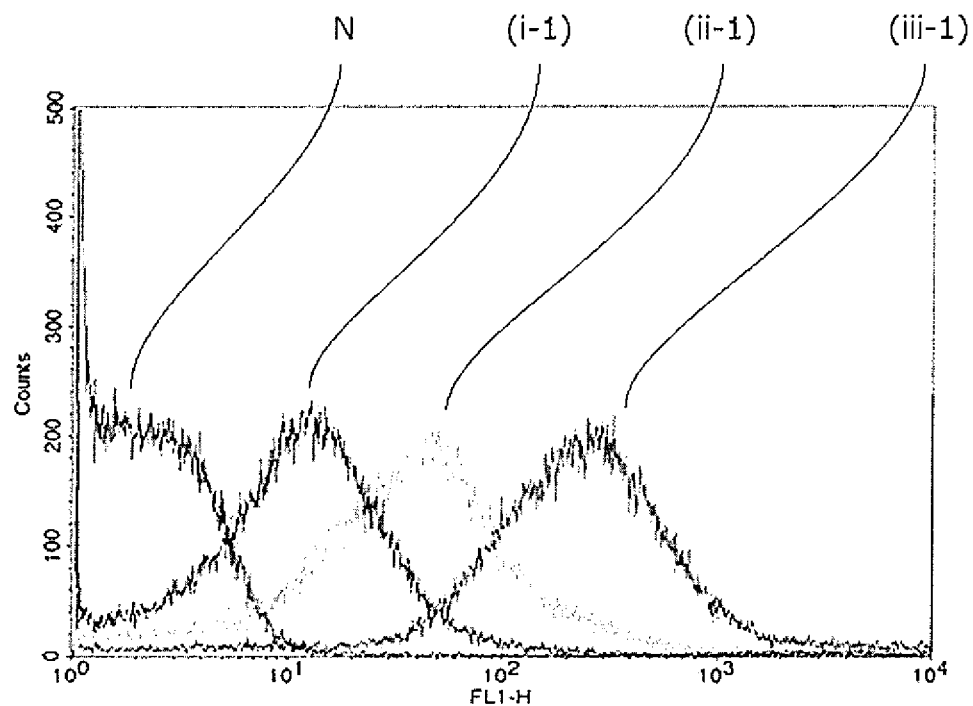
FIG. 2B is a graph illustrating the result of the FACS analysis in Production Example 2.

In FIG. 2B, "N" represents the result of the negative control (killed bacterium), "(i-1)" represents the result of the mutant E7 protein-expressed type lactic acid bacterium which had been cultured in MRSE with no addition of $NaHCO_3$ (pH 6.4) and killed, "(ii-1)" represents the result of the mutant E7 protein-expressed type lactic acid bacterium which had been cultured in MRSE with addition of 10 mM $NaHCO_3$ (pH 6.8) and killed, and "(iii-1)" represents the result of the mutant E7 protein-expressed type lactic acid bacterium which had been cultured in MRSE with addition of 25 mM NaHCO$_3$ (pH 7.1) and killed.

For the result of FIG. 2B, it was indicated that the expression amount of the mutant E7 protein on the surface of the bacterium was able to be modified by adjusting pH of the culture solution.

Figure 3A:
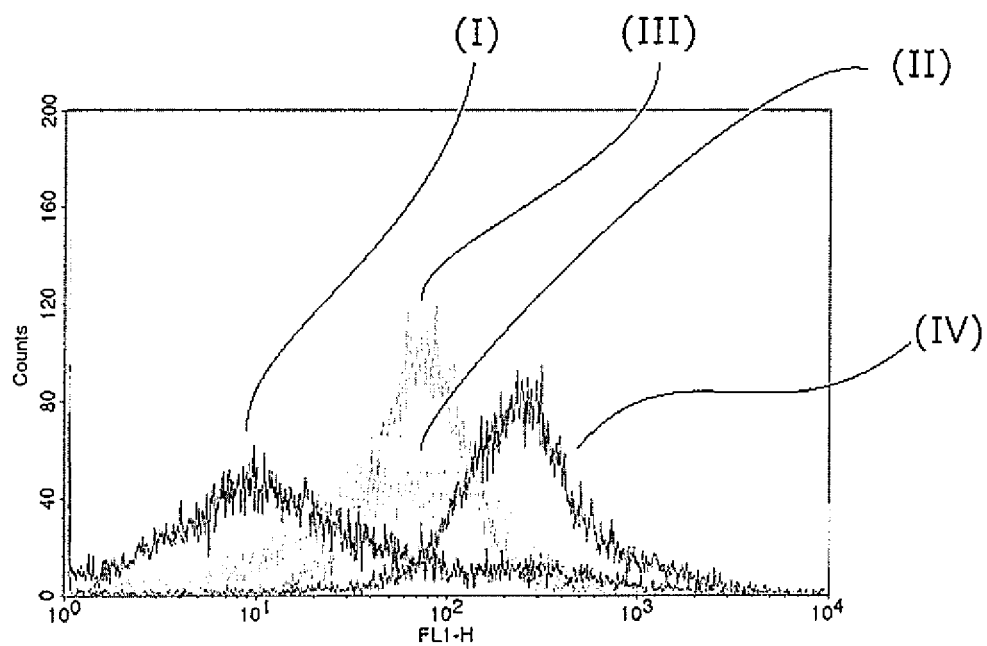
FIG. 3A is a graph illustrating the result of the FACS analysis (measurement condition: 525 of Voltage) in Test Example 1.
Figure 3B:
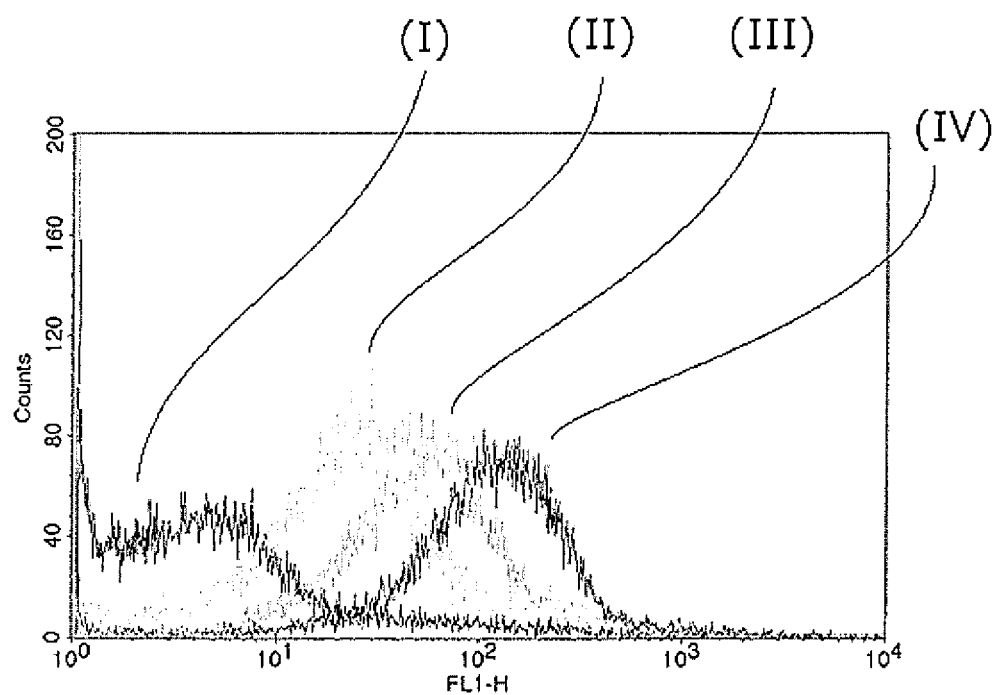
FIG. 3B is a graph illustrating the result of the FACS analysis (measurement condition: 600 of Voltage) in Test Example 1.

Test Example 1: Comparison of Amounts of Mutant E7 Proteins on Surfaces of Bacteria The below-described samples were subjected to the FACS analysis in the same manner as in the Production Example 1 to thereby compare amounts of the mutant E7 proteins on the surfaces of the bacteria per $1.0 \times 10^8$ lactic acid bacteria. The results are illustrated in FIGS. 3A and 3B.
<Sample>
(I) . . . The negative control in the Production Example 2 (killed bacteria);
(II) . . . The LacE7 preparation produced in the Comparative Production Example 1;
(III) . . . The mutant E7 protein-bound type lactic acid bacterium on which surface 0.03 µg of the mutant E7 protein was bound per $1.0 \times 10^8$ lactic acid bacteria (with TCA treatment) of (3) in the Production Example 1; and
(IV) . . . The mutant E7 protein-expressed type lactic acid bacterium which had been cultured in MRSE with addition of 25 mM NaHCO$_3$ (pH 7.1) and killed of (iii-1) in the Production Example 2.

In FIGS. 3A and 3B, "(I)" represents the result of the sample (I), "(II)" represents the result of the sample (II), "(III)" represents the result of the sample (III), and "(IV)" represents the result of the sample (IV).

For the result of FIG. 3A (measurement condition: 525 of Voltage), it was indicated that, in the existing LacE7 preparation, fluorescence intensity was broadly distributed, i.e., there were larger number of the lactic acid bacteria on which surfaces the mutant E7 proteins were not expressed. Also, for the result of FIG. 3B (measurement condition: 600 of Voltage), it was indicated that, in the existing LacE7 preparation, the mutant E7 protein on the surface of the bacterium was lower expressed.

Meanwhile, in the mutant E7 protein-expressed type lactic acid bacterium which had been cultured in MRSE with addition of 25 mM NaHCO$_3$ (pH 7.1) and killed of (iii-1) in the Production Example 2, the expression amount of the mutant E7 protein per $1.0 \times 10^8$ lactic acid bacteria was estimated to be about 0.3 µg.

Test Example 2: Anti-HPV Mucosal Immunity-Inducibility Test-1

An anti-HPV mucosal immunity-inducibility test was performed in the following manner using the LacE7 preparation produced in the Comparative Example 1.
<Immunization of Mouse>
Mice were orally immunized with the LacE7 preparation according to the procedure described in K. Adachi et al., Vaccine, 2010, vol. 28, pp. 2810-2817.
<<Oral Administration of LacE7 Preparation to Mouse>>
Six-week old female SPF C67BL mice (CLEA Japan, Inc.) were immunized with the LacE7 preparation through oral administration.

The LacE7 preparation (0.1 mg, 0.3 mg, or 1.0 mg per mouse) was administered for a total of 4 rounds at weeks 1, 2, 4, and 6. For all administration, the LacE7 preparation was suspended in 200 µL of PBS and administered via an intra-gastric tube after 3 hours of fasting once per day for consecutive five days every week.
<Collection of Intestine>
One week after the last inoculation of the LacE7 preparation (at week 7), the five mice to which the LacE7 preparation had been inoculated were dissected, from which intestines were collected. After feces were removed from the intestines, the inside of each of the intestinal tracts was washed with 10 mL of HBSS supplemented with a protease inhibitor.
<Preparation of Murine Mucosa Lymphocyte>
Each intestine was opened longitudinally and shaken vigorously in a PRMI1640 medium, which contained 10% by mass inactivated fetal bovine serum, 2 mM L-glutamine, 1 mM sodium pyruvate, 1× non-essential amino acids, and 50 mM 2-mercaptoethanol, supplemented with 10% by mass FBS, 100 unit/mL of penicillin and 100 µg/mL of streptomycin at 37° C. for 30 min. A cell suspension liquid was collected therefrom, passed through BD FALCON™ Cell strainer (BD Bioscience, USA) to thereby remove tissue debris, and then were subjected to discontinuous density gradient centrifugation in a 15 mL tube in which 40% by mass PERCOLL PLUS was layered on 70% by mass PERCOLL PLUS. About $10^7$ to about $10^8$ cells were layered thereon, followed by centrifugation at 600×g and room temperature for 20 min. As a result, mucosal lymphocytes (cell viability: 95%) were concentrated at the interface between the 70% by mass PERCOLL PLUS layer and the 40% by mass PERCOLL PLUS layer. About $5 \times 10^6$ to about $10 \times 10^6$ mucosa lymphocytes were obtained from each mouse.
<ELISPOT Assay>
Fifty microliters of a suspension of the intestinal mucosal lymphocytes ($5 \times 10^6$ cells/mL) was incubated for 24 hour at 37° C. together with antigen presenting cells.

According to a manufacture's instruction of MOUSE IFN-γELISPOT KIT (MABTECH AB, Sweden), 10 µL of a synthetic peptide (1 µg/mL) consisting of amino acids at positions 49 to 57 of the E7 protein which had been reported to be a CTL epitope for HPV16 E7 protein (SEQ ID No. 1), mitogen (40 ng/mL of phorbol myristate acetate plus 4 µg/mL of ionomycin), or a medium alone (control) were added dropwise to a 96-well plate (for example, ELIIP plate, Millipore, USA) coated with anti-mouse IFN-γ antibodies. The number of IFN-γ-positive spots on the 96-well plate was analyzed with a fully automated computer assisted video imaging analysis system, KS ELISPOT (Carl Zeiss Vision, Germany).
<Statistical Analysis>
ELISPOT data were represented as means±standard deviations. These values or relative values were compared between immunization groups (5 mice/group) using a two-sided Student's t-test. A p-value of <0.05 was considered to be significant.

Figure 4:
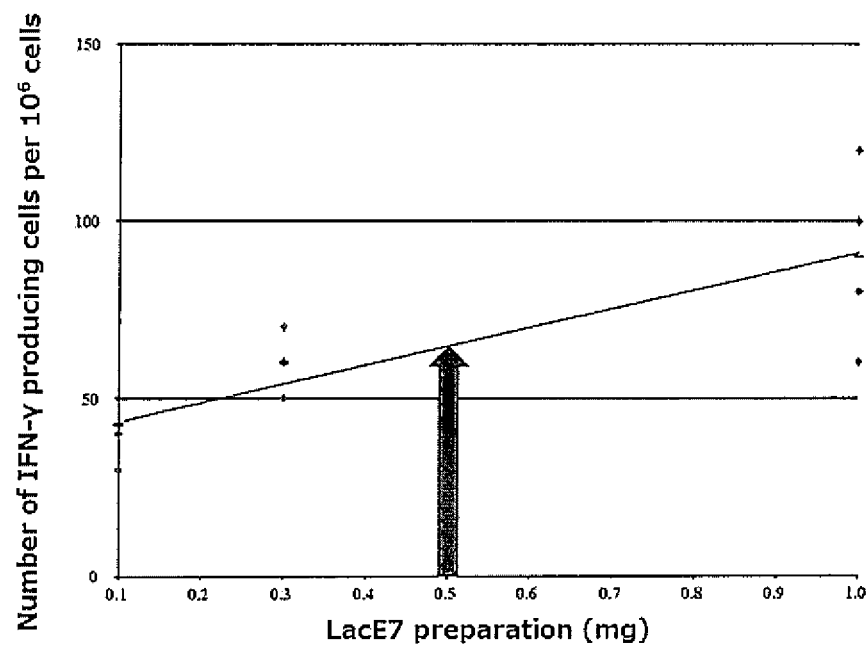
FIG. 4 is a graph illustrating the result of the ELISPOT assay of Test Example 2.

The results of Test Example 2 are illustrated in FIG. 4.

As evident from FIG. 4, the number of IFN-γ-producing cells per $10^6$ cells was increased depending on the administered amount.

Also, for the results of FIG. 4, the number of IFN-γ-producing cells per $10^6$ cells was calculated to be 65.8 cells in the case where 0.5 mg of the LacE7 preparation was administered (as indicated by the arrow in FIG. 4).

Test Example 3: Anti-HPV Mucosal Immunity-Inducibility Test-2

The anti-HPV mucosal immunity-inducibility test was performed in the same manner as in Test Example 2, except that each of the below-described samples was administrated at 0.5 mg/mouse.

<Sample>

Sample-1: The mutant E7 protein-bound type lactic acid bacterium on which surface 0.3 µg of the mutant E7 protein was bound per $1.0 \times 10^8$ lactic acid bacteria (with TCA treatment) of (1) in the Production Example 1;

Sample-2: The mutant E7 protein-bound type lactic acid bacterium on which surface 0.09 µg of the mutant E7 protein was bound per $1.0 \times 10^8$ lactic acid bacteria (without TCA treatment) of (6) in the Production Example 1;

Sample-3: The mutant E7 protein-bound type lactic acid bacterium on which surface 0.3 µg of the mutant E7 protein was bound per $1.0 \times 10^8$ lactic acid bacteria (without TCA treatment) of (5) in the Production Example 1;

Sample-4: The mutant E7 protein-expressed type lactic acid bacterium which had been cultured in MRSE with addition of 25 mM $NaHCO_3$ (pH 7.1) and not killed of (iii-2) in the Production Example 2; and Sample-5: The mutant E7 protein-expressed type lactic acid bacterium which had been cultured in MRSE with addition of 25 mM $NaHCO_3$ (pH 7.1) and killed of (iii-1) in the Production Example 2.

Figure 5:
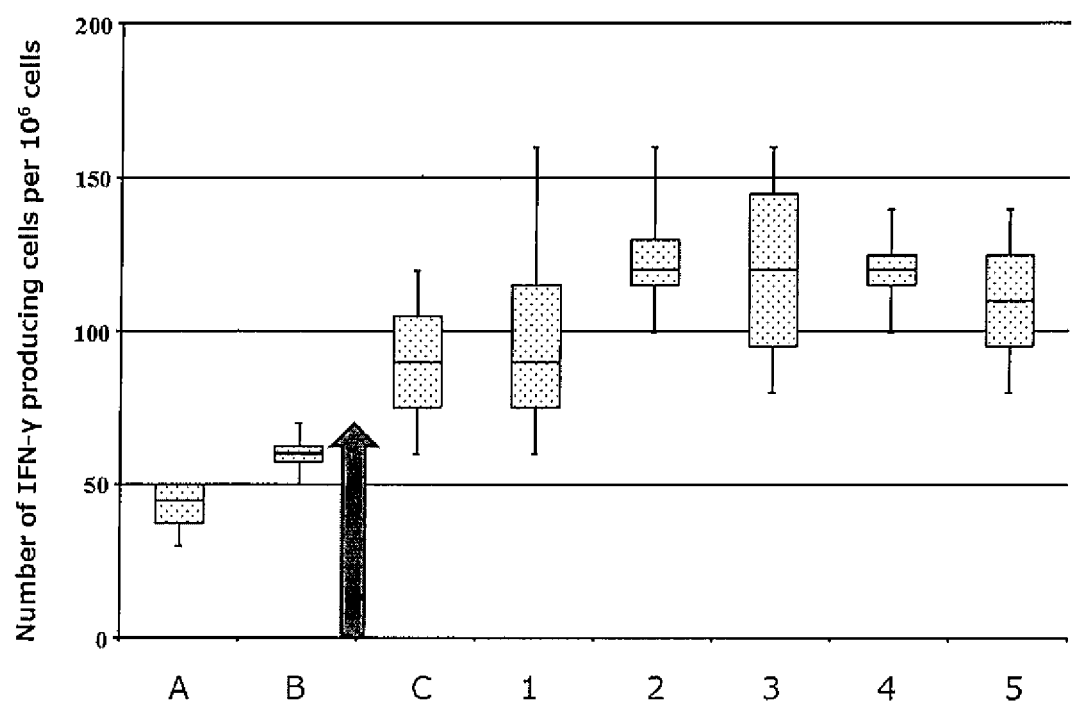
FIG. 5 is a graph illustrating the result of the ELISPOT assay of Test Example 3.

The results are illustrated in FIG. 5. In FIG. 5, the numbers 1 to 5 on the horizontal axis represent the sample numbers.

In FIG. 5, the results of the Test Example 2 are also illustrated. In FIG. 5, A represents the result in the case where the LacE7 preparation was administered at 0.1 mg/mouse in the Test Example 2, B represents the result in the case where the LacE7 preparation was administered at 0.3 mg/mouse in the Test Example 2, and C represents the result in the case where the LacE7 preparation was administered at 1.0 mg/mouse in the Test Example 2.

The arrow in FIG. 5 represents the number of IFN-γ-producing cells per $10^6$ cells in the case where the LacE7 preparation was administered at 0.5 mg/mouse calculated from the results of the Test Example 2.

For the results of FIG. 5, it was indicated that the Samples-1 to 5, which were the mutant E7 protein-bound type lactic acid bacterium or the mutant E7 protein-expressed type lactic acid bacterium of the present invention, had a more excellent anti-HPV immunity-inducibility than the LacE7 preparation, which was the known preparation, administered in the same amount as the Samples.

In particular, it was indicated that the anti-HPV immunity-inducibility of the Samples-2 to 5 was very excellent, i.e., about twice as high as that of the LacE7 preparation, which was the known preparation, administered in the same amount as the Samples.

In the clinical trial of human CIN3 patients using the known LacE7 preparation performed by the present inventors, the number of IFN-γ-producing cells in the cured group was compared with that of the non-cured group. It was demonstrated that the number of IFN-γ-producing cells in the cured group was about twice as many as that in the non-cured group (K. Kawana et al., "Oral vaccination against HPV E7 for treatment of cervical intraepithelial neoplasia grade 3 (CIN3) elicits E7-specific mucosal immunity in the cervix of CIN3 patients.", Vaccine, 2014 Oct. 29; 32 (47): 6233-9.).

Therefore, based on the fact that the number of IFN-γ-producing cells in those who were administered with the mutant E7 protein-bound type lactic acid bacterium or the mutant E7 protein-expressed type lactic acid bacterium of the present invention was about twice as many as that in those who were administered with the known LacE7 preparation in the same amount, it is expected that the lactic acid bacterium of the present invention would significantly improve the clinical effect (response rate).

Aspects of the present invention are, for example, as follows.

<1> A lactic acid bacterium-containing composition including a lactic acid bacterium having a human papillomavirus (HPV) E7 protein-derived polypeptide on a surface thereof, wherein the HPV E7 protein-derived polypeptide is included in an amount of 0.03 µg to 1.0 µg per $1 \times 10^8$ lactic acid bacteria.

<2> The lactic acid bacterium-containing composition according to <1>, wherein the HPV E7 protein-derived polypeptide is bound on the surface of the lactic acid bacterium.

<3> The lactic acid bacterium-containing composition according to <1>, wherein the HPV E7 protein-derived polypeptide is expressed on the surface of the lactic acid bacterium.

<4> The lactic acid bacterium-containing composition according to any one of <1> to <3>, wherein the lactic acid bacterium is *Lactobacillus casei*.

<5> A therapeutic oral pharmaceutical composition for at least one of an HPV infectious disease and an HPV-associated tumor, the composition including the lactic acid bacterium-containing composition according to any one of <1> to <4>.

<6> The therapeutic oral pharmaceutical composition for at least one of an HPV infectious disease and an HPV-associated tumor according to <5>, wherein the composition is used for treating at least one of a cervical intraepithelial neoplasia and an early-stage cervical cancer.

<7> A mucosal immunity-inducing agent including the lactic acid bacterium-containing composition according to any one of <1> to <4>.

The invention claimed is:

1. A lactic acid bacterium-containing composition comprising
a lactic acid bacterium having a human papillomavirus (HPV) E7 protein-derived polypeptide on a surface thereof,
wherein the HPV E7 protein-derived polypeptide is fused with an anchor protein cA derived from AcmA to form a fusion protein or is expressed from a sequence of a nucleic acid coding for the HPV E7 protein-derived polypeptide linked to an anchor gene prtP,
wherein the HPV E7 protein-derived polypeptide is included in an amount of 0.03 µg to 1.0 µg per 1×10$^8$ lactic acid bacteria on the surface of the bacterium.

2. The lactic acid bacterium-containing composition according to claim 1, wherein the HPV E7 protein-derived polypeptide is bound on the surface of the lactic acid bacterium.

3. The lactic acid bacterium-containing composition according to claim 1, wherein the HPV E7 protein-derived polypeptide is expressed on the surface of the lactic acid bacterium.

4. The lactic acid bacterium-containing composition according to claim 1, wherein the lactic acid bacterium is *Lactobacillus casei*.

5. A therapeutic oral pharmaceutical composition for at least one of an HPV infectious disease and an HPV-associated tumor, the composition comprising
a lactic acid bacterium-containing composition comprising a lactic acid bacterium having a human papillomavirus (HPV) E7 protein-derived polypeptide on a surface thereof,
wherein the HPV E7 protein-derived polypeptide is fused with an anchor protein cA derived from AcmA to form a fusion protein, or is expressed from a sequence of a nucleic acid coding for the HPV E7 protein-derived polypeptide linked to an anchor gene prtP,
wherein the HPV E7 protein-derived polypeptide is included in an amount of 0.03 µg to 1.0 µg per 1×10$^8$ lactic acid bacteria on the surface of the bacterium.

6. The therapeutic oral pharmaceutical composition for at least one of an HPV infectious disease and an HPV-associated tumor according to claim 5, wherein the composition is used for treating at least one of a cervical intraepithelial neoplasia and an early-stage cervical cancer.

7. A mucosal immunity-inducing agent comprising
a lactic acid bacterium-containing composition comprising a lactic acid bacterium having a human papillomavirus (HPV) E7 protein-derived polypeptide on a surface thereof,
wherein the HPV E7 protein-derived polypeptide is fused with an anchor protein cA derived from AcmA to form a fusion protein, or is expressed from a sequence of a nucleic acid coding for the HPV E7 protein-derived polypeptide linked to an anchor gene prtP,
wherein the HPV E7 protein-derived polypeptide is included in an amount of 0.03 µg to 1.0 µg per 1×10$^8$ lactic acid bacteria on the surface of the bacterium.

8. The lactic acid bacterium-containing composition according to claim 2, wherein the lactic acid bacterium is *Lactobacillus casei*.

9. The lactic acid bacterium-containing composition according to claim 3, wherein the lactic acid bacterium is *Lactobacillus casei*.

10. The therapeutic oral pharmaceutical composition for at least one of an HPV infectious disease and an HPV-associated tumor according to claim 5, wherein the HPV E7 protein-derived polypeptide is bound on the surface of the lactic acid bacterium.

11. The therapeutic oral pharmaceutical composition for at least one of an HPV infectious disease and an HPV-associated tumor according to claim 5, wherein the HPV E7 protein-derived polypeptide is expressed on the surface of the lactic acid bacterium.

12. The therapeutic oral pharmaceutical composition for at least one of an HPV infectious disease and an HPV-associated tumor according to claim 5, wherein the lactic acid bacterium is *Lactobacillus casei*.

13. The mucosal immunity-inducing agent according to claim 7, wherein the HPV E7 protein-derived polypeptide is bound on the surface of the lactic acid bacterium.

14. The mucosal immunity-inducing agent according to claim 7, wherein the HPV E7 protein-derived polypeptide is expressed on the surface of the lactic acid bacterium.

15. The mucosal immunity-inducing agent according to claim 7, wherein the lactic acid bacterium is *Lactobacillus casei*.

16. The lactic acid bacterium-containing composition according to claim 1, wherein the anchor gene prtP is downstream of the promoter sequence of S-layer protein.

17. The lactic acid bacterium-containing composition according to claim 1, wherein the lactic acid bacterium is subjected to a heat treatment with PBS.

18. The therapeutic oral pharmaceutical composition for at least one of an HPV infectious disease and an HPV-associated tumor according to claim 5, wherein the anchor gene prtP is downstream of the promoter sequence of S-layer protein.

19. The therapeutic oral pharmaceutical composition for at least one of an HPV infectious disease and an HPV-associated tumor according to claim 5, wherein the lactic acid bacterium is subjected to a heat treatment with PBS.

20. The mucosal immunity-inducing agent according to claim 7, wherein the anchor gene prtP is downstream of the promoter sequence of S-layer protein.

21. The mucosal immunity-inducing agent according to claim 7, wherein the lactic acid bacterium is subjected to a heat treatment with PBS.

* * * * *